(12) United States Patent
Lee

(10) Patent No.: US 7,160,508 B2
(45) Date of Patent: Jan. 9, 2007

(54) PERSONAL CARE PRODUCTS HAVING ELASTOMERIC PORTIONS

(75) Inventor: Jason Lee, Acton, MA (US)

(73) Assignee: The Gillette Company, Boston, MA (US)

( * ) Notice: Subject to any disclaimer, the term of this patent is extended or adjusted under 35 U.S.C. 154(b) by 238 days.

(21) Appl. No.: 09/946,913

(22) Filed: Sep. 5, 2001

(65) Prior Publication Data

US 2003/0044313 A1    Mar. 6, 2003

(51) Int. Cl.
A61L 2/16       (2006.01)
A01N 25/34      (2006.01)

(52) U.S. Cl. .............................. 422/28; 424/411

(58) Field of Classification Search ............... 424/411; 422/28
See application file for complete search history.

(56) References Cited

U.S. PATENT DOCUMENTS

| | | | |
|---|---|---|---|
| 4,086,297 A * | 4/1978 | Rei et al. ............. | 524/330 |
| 4,265,899 A * | 5/1981 | Lewis et al. ........... | 514/372 |
| 4,386,620 A | 6/1983 | Handler | |
| 4,542,169 A | 9/1985 | Costerton | |
| 5,787,586 A | 8/1998 | Apprille, Jr. et al. | |
| 6,026,824 A * | 2/2000 | Gueret ............... | 132/218 |
| 6,076,223 A | 6/2000 | Dair et al. | |
| 6,108,847 A | 8/2000 | Cueman et al. | |
| 6,117,119 A | 9/2000 | Gould | |
| 6,138,315 A | 10/2000 | Schmitt et al. | |
| 6,185,779 B1 * | 2/2001 | Kramer ............... | 15/167.1 |
| 2002/0169230 A1 * | 11/2002 | Redlich et al. ......... | 523/122 |
| 2003/0035953 A1 | 2/2003 | Weihrauch ............. | 428/375 |
| 2005/0131100 A1 * | 6/2005 | Herbst et al. .......... | 523/122 |

FOREIGN PATENT DOCUMENTS

| | | | |
|---|---|---|---|
| GB | 1160432 | * | 8/1969 |
| WO | WO98/07349 | | 2/1998 |
| WO | WO 98/51189 | | 11/1998 |
| WO | WO 99/35911 A1 | * | 7/1999 |

* cited by examiner

Primary Examiner—E. Leigh McKane
(74) Attorney, Agent, or Firm—Fish & Richardson P.C.

(57) ABSTRACT

A personal care product is provided comprising a handle, and, mounted on the handle, an elastomeric portion comprising an elastomeric material and an antimicrobial agent. Methods are provided for inhibiting mold growth on personal care products that include elastomeric portions.

13 Claims, 2 Drawing Sheets

PERSONAL CARE PRODUCTS HAVING ELASTOMERIC PORTIONS

TECHNICAL FIELD

This invention relates to personal care products having elastomeric portions, for example elastomeric gripping areas.

BACKGROUND

Personal care products such as razors and toothbrushes often include elastomeric portions, such as elastomeric gripping areas, to improve user comfort and to provide desirable aesthetic qualities.

When such products are stored in humid conditions, for example in a user's shower area, the elastomeric portions of the products may exhibit discoloration, which may be unattractive to the user.

SUMMARY

The inventors have found that, by incorporating an antifungal agent into the elastomer, discoloration of the elastomeric portions of personal care products can be inhibited or, in preferred implementations, eliminated entirely.

In one aspect, the invention features a personal care product comprising a handle, and, mounted on the handle, an elastomeric portion comprising an elastomeric material and an antimicrobial agent.

Some implementations include one or more of the following features. The antimicrobial agent includes an isothiazolinone. The antimicrobial agent is thermally stable. The antimicrobial agent is present in a concentration of at least 500 ppm, preferably from about 700 to 2000 ppm. The elastomeric material includes a styrenic block copolymer, e.g., styrene-ethylene-butylene-styrene (SEBS). The antimicrobial agent has a minimum inhibitory concentration of less that 100 ppm. The antimicrobial agent includes 4,5-dichloro-2-n-octyl-4-isothiazolin-3-one. The product is selected from the group consisting of manual toothbrushes, razors, electric toothbrushes and electric shavers. The elastomeric portion includes a gripping portion. The antimicrobial agent exhibits both antifungal and antibacterial properties.

The invention also features a method of inhibiting mold growth on a personal care product having an elastomeric portion including adding an antimicrobial agent to the elastomeric portion.

The term "antimicrobial agent" refers to an agent that inhibits the growth of mold and/or bacteria.

The term "antifungal" refers to the ability to inhibit the growth of mold spores.

The term "personal care product" includes electric and manual toothbrushes, razors, electric shavers, holders for these products, and other products that are used in personal care and are generally stored in a bathroom area.

The term "handle" refers to any part of a product by which a user would typically grasp or hold the product.

Other features and advantages of the invention will be apparent from the description and drawings, and from the claims.

DETAILED DESCRIPTION

Figure 1:
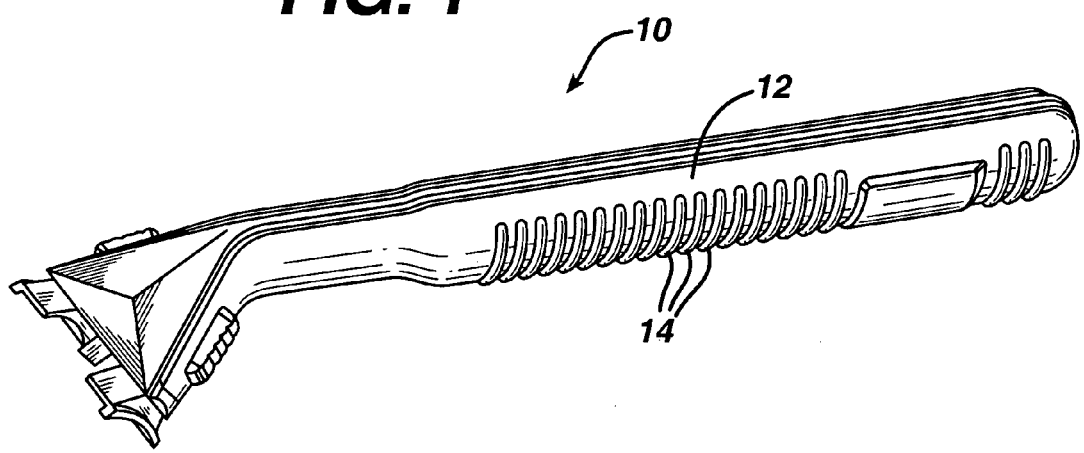
FIG. 1 is a perspective view of a razor.
Figure 2:
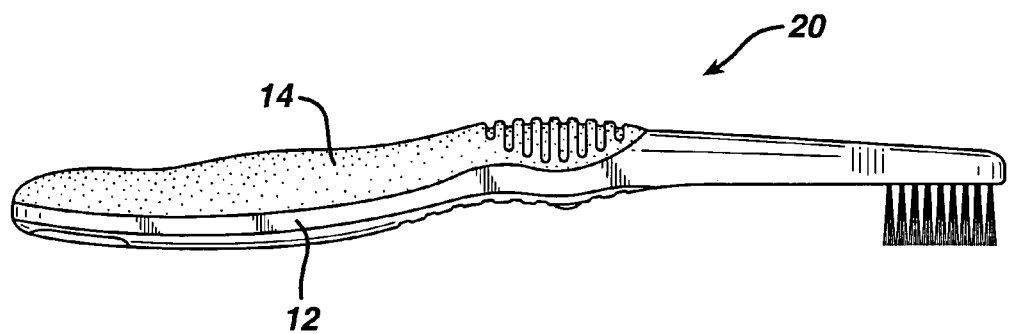
FIG. 2 is a perspective view of a toothbrush.
Figure 3:
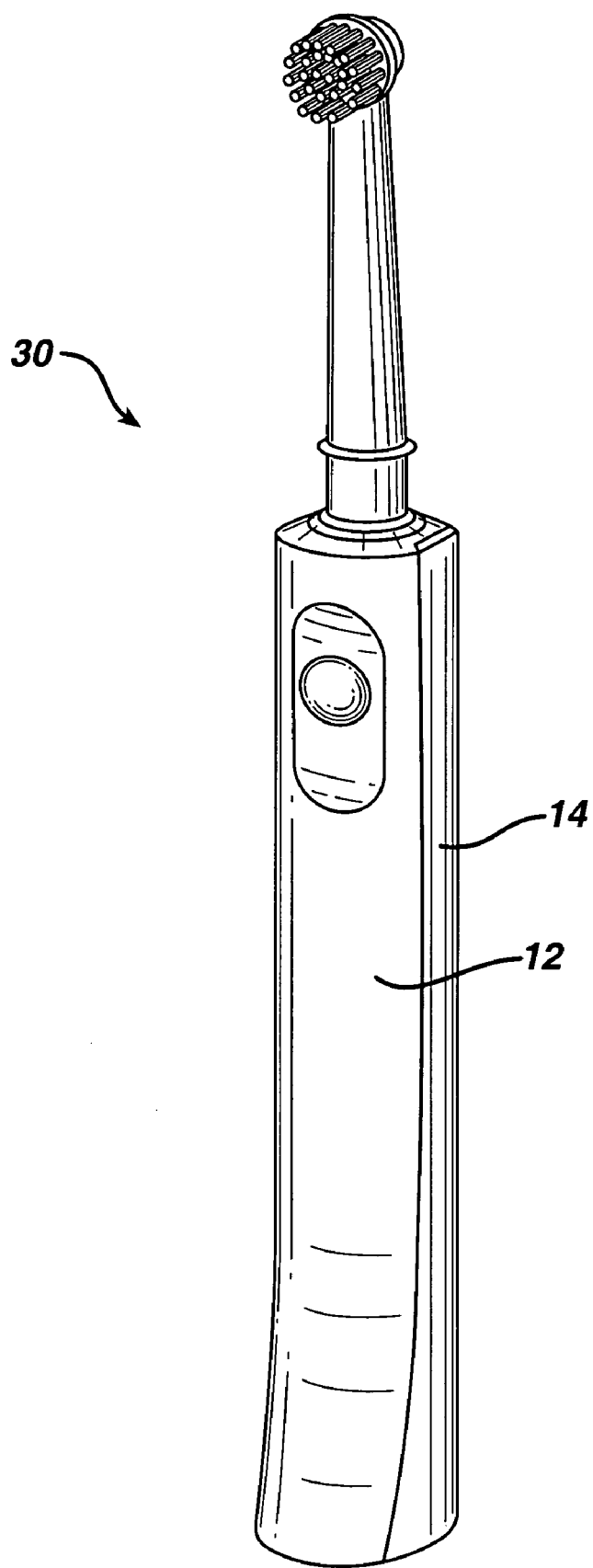
FIG. 3 is a perspective view of an electric toothbrush.

Referring to FIGS. 1–3, three examples of personal care products are illustrated: a razor 10 (FIG. 1), a manual toothbrush 20 (FIG. 2), and an electric toothbrush 30 (FIG. 3). Each product includes a handle 12 and, on the handle, one or more elastomeric gripping areas 14. Elastomeric gripping areas 14 are formed of an elastomeric material that includes an antimicrobial agent having antifungal properties.

Suitable materials for handle 12 include plastics that are sufficiently rigid so that the handle will not flex excessively during use. Suitable materials include high impact polystyrene, ABS, polypropylene, cellulose acetate proprionate and thermoplastic polyurethanes.

Suitable elastomeric materials include an elastomer or blend of elastomers. Elastomers suitable for use in gripping areas 14 are well known in the razor and toothbrush art. Generally, the elastomeric material includes one or more thermoplastic elastomers (TPEs). Suitable TPEs include thermoplastic vulcanates (rubber polyolefin blends), polyetheramides, polyesters, styrene-ethylene-butylene-styrene (SEBS) block copolymers, styrene-butadiene-styrene block copolymers, partially or fully hydrogenated styrene-butadiene-styrene block copolymers, styrene-isoprene-styrene block copolymers, partially or fully hydrogenated styrene-isoprene-styrene block copolymers, polyurethanes, polyolefin elastomers, polyolefin plastomers, styrenic based polyolefin elastomers, compatible mixtures thereof, and similar thermoplastic elastomers. Preferred TPEs include styrene-ethylene-butylene-styrene (SEBS) block copolymers, styrene-butadiene-styrene block copolymers, partially or fully hydrogenated styrene-butadiene-styrene block copolymers, styrene-isoprene-styrene block copolymers, and partially or fully hydrogenated styrene-isoprene-styrene block copolymers, commercially available from Shell under the tradename KRATON rubber. Particularly preferred are styrene-ethylene-butylene-styrene (SEBS) block copolymers available from Shell under the tradename "G-Type" KRATON rubbers. The aforementioned TPEs may be modified with fillers such as talc, and with oil, which will generally reduce the hardness of the elastomer, as is well known in the art. Other suitable elastomers include resilient urethanes and silicones.

Preferred elastomeric materials are durable enough to withstand use during the lifetime of the product the material is to be used in (e.g. a toothbrush or razor) without tearing or abrading, and hard enough to provide a secure-feeling grip, while also being sufficiently soft to provide a comfortable degree of cushioning during use. Preferred materials have a hardness of from about 3 to 90 Shore A, more preferably about 10 to 60 Shore A.

Preferred elastomeric materials will also adhere sufficiently strongly to the handle 12 so that the gripping areas 14 will not fall off during storage or use. Generally, elastomers having a polarity similar to that of the handle will adhere best. More polar elastomers seem more likely to support mold growth than less polar elastomers under similar conditions. Styrenic-based block copolymers, e.g., block copolymers sold under the tradename KRATON rubbers, that are modified to adhere to relatively polar handle materials generally support mold growth under the conditions normally found in household bathrooms.

Generally, for processing purposes the elastomers discussed above are compounded with a plasticizer, e.g., mineral oil, and a thermoplastic, e.g., polypropylene, and pelletized to form the elastomeric material. Inclusion of a plasticizer and a thermoplastic improves the flow of the elastomeric material during molding.

Suitable antimicrobial agents will inhibit the growth of mold on the elastomeric portions of the product during normal use and storage, with no deleterious effect on users of the product. Preferred antimicrobial agents are effective at relatively low concentrations. Preferably, when the antimicrobial is used at a concentration of 5% (total additive, including any carrier) or less in a styrenic block copolymer, when tested using ASTM Test Procedures G21-90, E1428-91 and G22-76 the block copolymer will exhibit no visible mold growth after 28 days. It is also preferred that the antimicrobial agent enable the elastomeric material to withstand multiple contaminations by mold spores without exhibiting mold growth. This capability can be measured by the Re-inoculation Protocol discussed in the Example below.

Preferred antimicrobial agents will inhibit mold growth at relatively low concentrations of antimicrobial agent, i.e., preferred antimicrobial agents will have a low "minimum inhibitory concentration" (MIC), measured as parts per million (ppm) concentration in sterile water and agar using the test procedure discussed below. If the MIC is high, a high concentration of antimicrobial agent will generally be necessary in order to obtain sufficient antifungal activity, resulting in increased cost and a potential adverse affect on the properties of the elastomeric material. For example, high concentrations of antifungal agent may tend to increase the hardness of the thermoplastic elastomer. Preferred antimicrobial agents have an MIC of less than about 100 ppm.

Minimum inhibitory concentration is measured by diluting the antimicrobial agent in sterile water to obtain a plurality of solutions having a range of concentrations. 1 ml of each of the solutions is added to 9 ml portions of molten agar to give a final volume of 10 ml, and immediately poured to form plates. After solidification, the plates are streaked with the following molds at concentrations of approximately $10^6$: *Aspergillus niger, Penicillum pinophilum, Chaetomium globosum, Trichoderma virens* (formerly *Gliocladium virens*), and *Aureobasidium pullulans*. The plates are incubated at 27±2° C. and analyzed for growth at 3, 5 and 7 days. The lowest concentration at which no growth is observed with the naked eye after 7 days is the MIC.

Generally, suitable antimicrobial agents will not deleteriously affect the aesthetic properties of the elastomeric material, e.g., by producing an undesirable color change when incorporated into the elastomeric material. Preferably, the antimicrobial agent does not adversely affect the mechanical properties or hardness of the elastomeric material, although some degree of change can generally be compensated for by adjusting the formulation.

Preferred antimicrobial agents are also thermally stable, i.e., able to withstand a temperature of 300° F. for at least 30 minutes without a significant decrease in the antimicrobial properties of the agent. More preferred antimicrobial agents are able to withstand a temperature of at least 400° F., most preferably at least 500° F., for at least 30 minutes. When incorporated into an elastomeric material, it is preferred that the antimicrobial agent be able to withstand at least 5 cycles of freeze/thaw testing, and at least 180 days at 45° C., without deterioration of antimicrobial properties, and with minimal migration of the antimicrobial agent to the surface of the elastomeric material. Freezing the elastomeric material at −10° C. for 2 days, then thawing for one day, constitutes one freeze thaw cycle. It is also generally preferred that the antimicrobial be shear stable, i.e., capable of withstanding the shear experienced during conventional elastomer compounding processes.

Suitable antimicrobial agents include isothiazolinones, e.g., 4,5-dichloro-2-n-octyl-4-isothiazolin-3-one ($C_{11}H_{17}CL_2NOS$; CAS Registration No. 64359-81-5). Isothiazolinones are commercially available, e.g., from Rohm & Haas Company. 4,5-dichloro-2-n-octyl-4-isothiazolin-3-one has an MIC of about 50 ppm, a molecular weight of 282.2, and is thermally stable.

In cases in which the antimicrobial agent raises toxicity concerns, the antimicrobial agent should be compatible with the elastomeric material that is used, so that minimal migration of the antimicrobial agent to the surface of the elastomeric portions will occur during normal use and storage. In the case of isothiazolinones, preferred antimicrobial agents will exhibit less than 1.5 µg/cm²/day migration. Mirgration may be measured by wiping the elastomer surface with a large cotton swab soaked in methanol, and then using HPLC to determine the concentration of the antimicrobial agent in the methanol. Some migration may be necessary in order for the antimicrobial to be active at the product surface, however the amount at the surface may be so low as to be virtually undetectable.

The preferred concentration of the antimicrobial agent in the elastomeric material will depend upon the particular antimicrobial agent and elastomeric material that are used. However, generally the concentration will be at least 500 ppm, preferably from about 700 to 2000 ppm. A suitable concentration can be determined based on the requirements of a particular application using the criteria discussed above. These concentrations are based on the active amount of the antimicrobial.

The antimicrobial is generally incorporated into the elastomeric material when the elastomeric material is compounded (the elastomer is pelletized with plasticizer and thermoplastic) as discussed above. Compounding is generally performed in a twin screw extruder, at a temperature of from about 300 to 500° F.

If desired, the antimicrobial agent may be incorporated into a carrier prior to addition into the elastomeric material, to facilitate measuring and mixing of the small amount of antimicrobial agent into the much larger amount of elastomeric material. Suitable carriers will be compatible with the antimicrobial agent and the elastomeric material, and will not deleteriously affect the final properties of the elastomeric portions. A suitable carrier is an ethylene vinyl acetate (EVA)/carbon monoxide copolymer that is commercially available from Dupont under the tradename Elvaloy.

Reinoculation Test Procedure

This procedure tests the ability of the antimicrobial to withstand multiple contaminations. Part A can provide information as to whether the antimicrobial was used up by the first inoculation. Part B can provide information on the ability of the antimicrobial to inhibit growth even though a substantial bio-burden is present.

Part A (Wash/Re-inoculate)
1. After completion of initial testing (inoculation and 28 day incubation per ASTM Method Mold Method G21), handles are removed from the incubator and placed in dilution bottles that contain a 1% shave gel solution. The bottles are capped and shaken vigorously for 1 minute. Handles are then allowed to soak for 10 minutes.
2. After the wash is complete the handles are rinsed. Handles are again place in dilution bottles containing sterile water. The bottles are capped and shaken vigorously for 1 minute. They are then allowed to soak for 10 minutes.

3. After the handles are rinsed they are allowed to dry for at least 30 minutes in a hood.
4. Handles are then re-inoculated and incubated for an additional 4 weeks.

Part B
1. After completion of initial testing, handles are removed from the incubators.
2. They are immediately re-inoculated
3. Handles are placed back into the incubators for an additional 4 weeks.

Other embodiments are within the scope of the following claims.

For example, while the elastomeric portions discussed above are gripping areas, the antifungal or antimicrobial agent may be used in any elastomeric portions of a personal care product, e.g., the fin guard of a razor cartridge or decorative elastomeric areas.

What is claimed is:

1. A personal care product comprising:
   a handle; and
   mounted on the handle, an elastomeric portion comprising an elastomeric material comprising a styrenic block copolymer comprising styrene-ethylene-butylene-styrene and an antimicrobial agent incorporated into the elastomeric material, the antimicrobial agent being is able to withstand a temperature of at least 400° F. for at least 30 minutes,
   wherein the personal care product is selected from the group consisting of manual toothbrushes, razors, electric toothbrushes and electric shavers, the antimicrobial agent comprises an isothiazolinone, and the antimicrobial agent is present in a concentration of from 500 ppm to 2000 ppm.

2. The personal care product of claim 1 wherein the antimicrobial agent is present in a concentration of from about 700 ppm to 2000 ppm.

3. The personal care product of claim 1 wherein the antimicrobial agent has a minimum inhibitory concentration of less than 100 ppm.

4. The personal care product of claim 1 wherein the antimicrobial agent comprises 4,5-dichloro-2-n-octyl-4-isothiazolin-3-one.

5. The personal care product of claim 1 wherein the antimicrobial agent exhibits both antifungal and antibacterial properties.

6. The personal care product of claim 1 wherein the elastomeric portion includes a gripping portion.

7. The personal care product of claim 1 wherein the antimicrobial agent is able to withstand a temperature of at least 500° F. for at least 30 minutes.

8. A method of inhibiting mold growth on a personal care product having an elastomeric portion comprising a styrenic block copolymer comprising styrene-ethylene-butylene-styrene, the method comprising incorporating an antimicrobial agent into the elastomeric portion in a concentration of from 500 ppm to 2000 ppm, wherein the antimicrobial agent comprises an isothiazolinone and is able to withstand a temperature of at least 400° F. for at least 30 minutes, and the personal care product is selected from the group consisting of manual toothbrushes, razors, electric toothbrushes and electric shavers.

9. The method of claim 8 comprising adding the antimicrobial agent in a concentration of from about 700 ppm to 2000 ppm.

10. The method of claim 8 further comprising selecting an antimicrobial agent having a minimum inhibitory concentration of less than 100 ppm.

11. The method of claim 8 wherein the antimicrobial agent comprises 4,5-dichloro-2-n-octyl-4-isothiazolin-3-one.

12. The method of claim 8 wherein the antimicrobial agent exhibits both antifungal and antibacterial properties.

13. The method of claim 8 wherein the antimicrobial agent is able to withstand a temperature of at least 500° F. for at least 30 minutes.

* * * * *

UNITED STATES PATENT AND TRADEMARK OFFICE
CERTIFICATE OF CORRECTION

PATENT NO. : 7,160,508 B2 Page 1 of 1
APPLICATION NO. : 09/946913
DATED : January 9, 2007
INVENTOR(S) : Jason Lee It is certified that error appears in the above-identified patent and that said Letters Patent is hereby corrected as shown below:

In claim 1, line 25, after "being", delete "is".

Signed and Sealed this

Sixth Day of May, 2008

JON W. DUDAS
*Director of the United States Patent and Trademark Office*